(12) United States Patent
Mou et al.

(10) Patent No.: US 11,442,052 B2
(45) Date of Patent: *Sep. 13, 2022

(54) VOC DETECTING AND WARNING METHOD

(71) Applicant: Microjet Technology Co., Ltd., Hsinchu (TW)

(72) Inventors: Hao-Jan Mou, Hsinchu (TW); Ta-Wei Hsueh, Hsinchu (TW); Li-Pang Mo, Hsinchu (TW); Chi-Feng Huang, Hsinchu (TW); Yung-Lung Han, Hsinchu (TW); Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 861 days.

This patent is subject to a terminal disclaimer.

(21) Appl. No.: 16/211,813

(22) Filed: Dec. 6, 2018

(65) Prior Publication Data

US 2019/0195850 A1 Jun. 27, 2019

(30) Foreign Application Priority Data

Dec. 25, 2017 (TW) .................................. 106145551

(51) Int. Cl.
*G01N 33/00* (2006.01)
*F16K 17/36* (2006.01)
*F24F 110/66* (2018.01)

(52) U.S. Cl.
CPC ......... *G01N 33/0063* (2013.01); *F16K 17/36* (2013.01); *G01N 33/0011* (2013.01);
(Continued)

(58) Field of Classification Search
CPC . F04B 43/046; F04B 43/043; G01N 33/0063; G01N 33/0011; G01N 33/0047;
(Continued)

(56) References Cited

U.S. PATENT DOCUMENTS 10,845,274 B2 * 11/2020 Richter ............... G01N 33/0014
2016/0076530 A1 * 3/2016 Chen ..................... F04B 45/047
417/413.2
(Continued)

FOREIGN PATENT DOCUMENTS

TW M455143 U1 6/2013
TW M552163 U 11/2017
(Continued)

OTHER PUBLICATIONS

Extended European Search Report, dated Jun. 28, 2019, for European Application No. 18210313.5.
(Continued)

*Primary Examiner* — Leslie J Evanisko
*Assistant Examiner* — Leo T Hinze
(74) *Attorney, Agent, or Firm* — Birch, Stewart, Kolasch & Birch, LLP

(57) ABSTRACT

A VOC detecting and warning method is provided. Firstly, an actuating-and-sensing module having a gas transportation actuator and a gas sensor is provided. Then, the gas transportation actuator guides a specified amount of gas to the gas sensor for obtaining plural monitored values, each of which is generated according to a result of detecting volatile organic compounds of the gas in each monitoring time interval by the gas sensor. All the monitored values obtained in a unit time period are added together and calculated, so that an average comparison value is obtained. If the average comparison value is determined greater than an injury threshold defined according to the VOC inhalation amount affecting the health of a human body, the actuating-and-sensing module issues a warning notification to notify the user to take protective measures.

13 Claims, 5 Drawing Sheets

(52) U.S. Cl.
CPC ...... *G01N 33/0047* (2013.01); *F24F 2110/66* (2018.01); *G01N 2033/0068* (2013.01)

(58) Field of Classification Search
CPC ............. G01N 2033/0068; F16K 17/36; F24F 2110/66
See application file for complete search history.

(56) References Cited

U.S. PATENT DOCUMENTS

| | | | | |
|---|---|---|---|---|
| 2016/0327532 | A1* | 11/2016 | Bather | G01N 33/0009 |
| 2017/0248514 | A1* | 8/2017 | Pavey | G01N 33/0036 |
| 2019/0187115 | A1* | 6/2019 | Bartosz | G08B 21/14 |

FOREIGN PATENT DOCUMENTS

| | | |
|---|---|---|
| TW | M552166 U | 11/2017 |
| TW | M553418 U | 12/2017 |

OTHER PUBLICATIONS

Author Unknown, "Indoor Environment Testing and Training Guidance," [online], Mar. 23, 2021, 6 pages total, with an English translation.

European Office Action dated Dec. 13, 2021 in Application No. 18 210 313.5-1001.

\* cited by examiner

VOC DETECTING AND WARNING METHOD

FIELD OF THE INVENTION

The present disclosure relates to a VOC detecting and warning method, and more particularly, an actuating-and-sensing module is utilized in the VOC detecting and warning method. The actuating-and-sensing module sucks gas therein and monitors volatile organic compounds of the gas.

BACKGROUND OF THE INVENTION

Recently, the air pollution problem becomes more and more serious. Consequently, people pay much attention to the methods of avoiding the harmfulness of various pollutants in the air. As known, volatile organic compounds (VOCs) are the common pollutants that are present in the air. The VOCs are in a gaseous form at room temperature and have strong volatility. For example, the VOCs include formaldehyde, toluene, xylene, ethylbenzene, propylene benzene, and so on. In addition to the exhaust gases from fuel combustion and vehicle transportation, the sources of the VOCs are diverse. For example, the VOCs are often dispersed in indoor environments through construction and decorative materials such as paints, coatings and adhesives. The VOCs may cause damage to the human bodies over the years. If the concentration of the VOCs in a room exceeds a specific concentration, people feel headache, nausea, vomit and limb weakness in a short time. In severe cases, people may have convulsions, coma and memory loss. Moreover, the VOCs harm people's livers, kidneys, brains and nervous systems, and they also contain many carcinogens.

However, the current technologies of detecting the VOCs still have some drawbacks. For example, in case that the volume of the detection device is small, the detection device is usually unable to immediately and accurately detect the VOCs. In addition, there is no detection device on the present market that can be carried and warn the user in real time when the amount of the VOCs in the environment reaching a hazard level is detected.

Therefore, there is a need of an improved VOC detecting and warning method in order to overcome the drawbacks of the conventional technologies that the accuracy of detecting the VOCs is low and fails to warn the user in real time.

SUMMARY OF THE INVENTION

An object of the present disclosure provides a VOC detecting and warning method, which utilizes a gas transportation actuator of an actuating-and-sensing module to guide the gas to a gas sensor of the actuating-and-sensing module. Then, the gas sensor detects the VOCs of the gas and generates a monitored value according to a result of detection in each monitoring time interval. All the monitored values obtained in a unit time period are accumulated and calculated to obtain an average comparison value. Then, the average comparison value is compared with an injury threshold that is defined according to the VOC inhalation amount affecting the health of a human body. If the average comparison value is greater than the injury threshold, the actuating-and-sensing module issues a warning notification to warn the user. Since the gas is guided to the gas sensor, the accuracy of the VOC detection is increased. In addition, once it is determined that the amount of VOCs in the environment has reached a hazard level, the user is warned in real time. Therefore, the drawbacks of the conventional technologies that the accuracy of detecting the VOCs is low and fails to warn the user in real time can be addressed.

In accordance with an aspect of the present disclosure, a VOC detecting and warning method is provided. Firstly, an actuating-and-sensing module having a gas transportation actuator and a gas sensor is provided. Then, the gas transportation actuator guides a specified amount of gas to the gas sensor, and the gas sensor generates a monitored value according to a result of detecting volatile organic compounds of the gas in each monitoring time interval. All the monitored values obtained in a unit time period are accumulated and calculated, so that an average comparison value is obtained. If the average comparison value is determined greater than an injury threshold, which is defined according to the VOC inhalation amount affecting the health of a human body, the actuating-and-sensing module issues a warning notification to notify the user to take protective measures.

In an embodiment, the actuating-and-sensing module further includes a microprocessor and a transmission module. The microprocessor processes the monitored values to generate output data and controls the gas transportation actuator to actuate. The transmission module transmits the output data to a connection device, so that information carried by the output data is displayed, stored and transmitted by the connection device.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
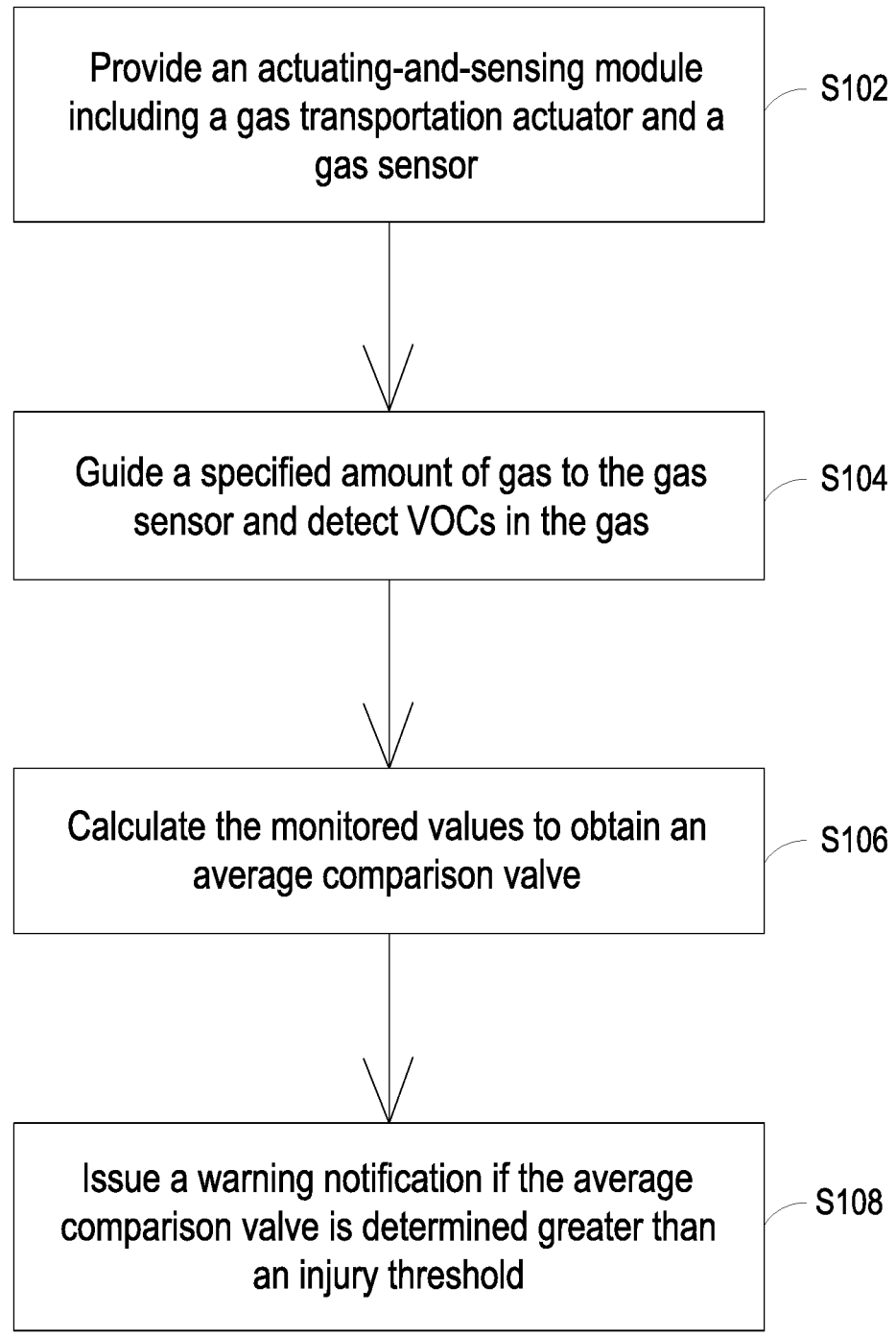
FIG. 1 is a flowchart illustrating a VOC detecting and warning method according to an embodiment of the present disclosure.
Figure 2:
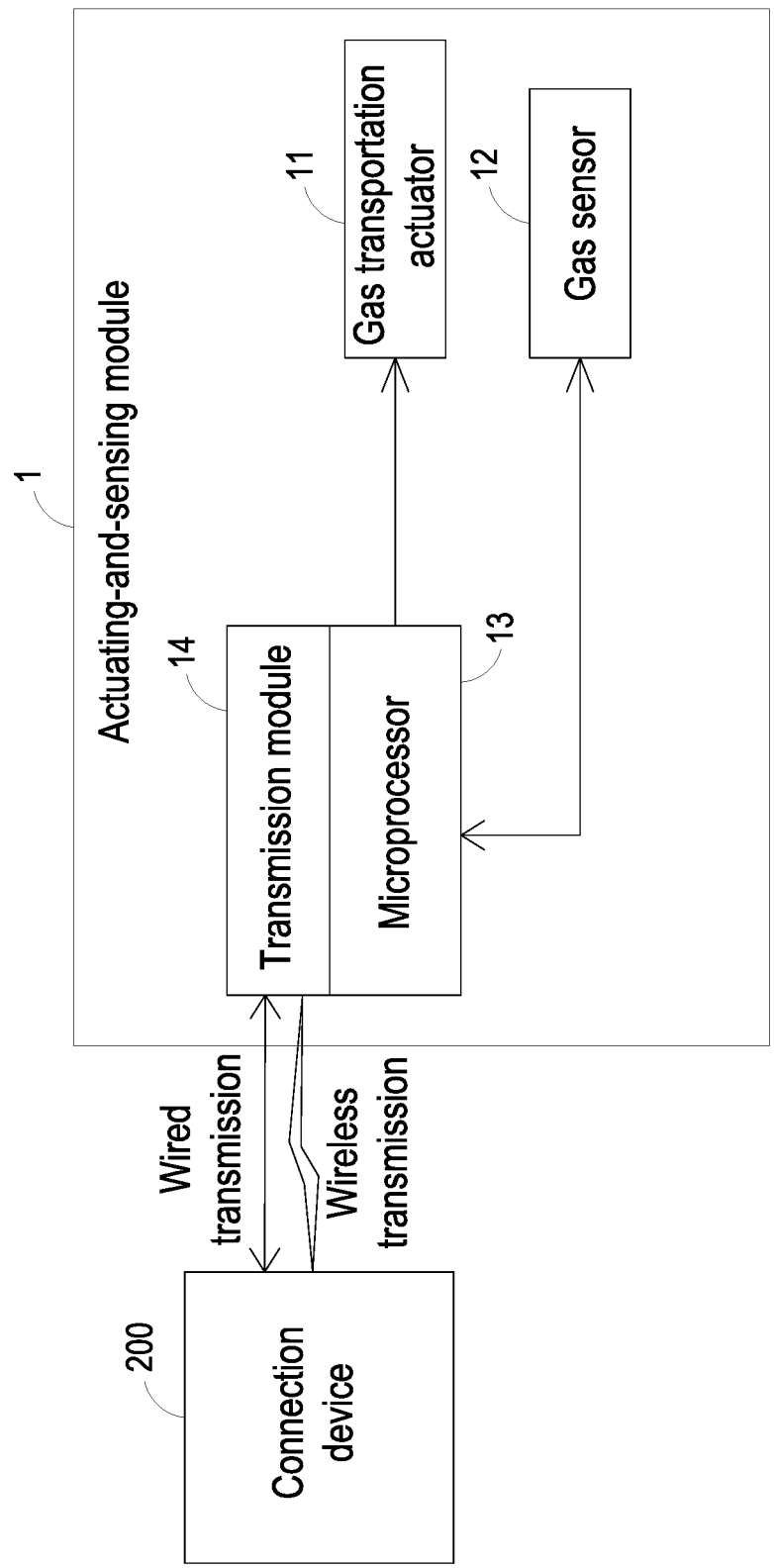
FIG. 2 is a schematic functional block diagram illustrating an actuating-and-sensing module for implementing the VOC detecting and warning method.

Please refer FIGS. 1 and 2. A VOC detecting and warning method is provided in the present disclosure. The method is implemented by employing at least one actuating-and-sensing module 1, at least one gas sensor 12, at least one gas transportation actuator 11, at least one monitored value, at least one average comparison value, at least one unit time period, at least one injury threshold and at least one warning notification. The numbers of the actuating-and-sensing module 1, the gas sensor 12, the gas transportation actuator 11, the monitored value, the average comparison value, the unit time period, the injury threshold and the warning notification are exemplified by one for each respectively in the following embodiments but not limited thereto. It is noted that each of the actuating-and-sensing module 1, the gas sensor 12, the gas transportation actuator 11, the monitored value, the average comparison value, the unit time period, the injury threshold and the warning notification can also be provided in plural numbers.

Please refer to FIGS. 1 and 2. FIG. 1 is a flowchart illustrating a VOC detecting and warning method according to an embodiment of the present disclosure. FIG. 2 is a schematic functional block diagram illustrating an actuating-and-sensing module for implementing the VOC detecting and warning method. Firstly, in a step S102, an actuating-and-sensing module 1 is provided. As shown in FIG. 2, the actuating-and-sensing module 1 includes a gas transportation actuator 11 and a gas sensor 12. In this embodiment, the actuating-and-sensing module 1 further includes a microprocessor 13 and a transmission module 14, but not limited thereto. When the gas transportation actuator 11 is enabled, a pressure gradient is generated to drive the gas to flow in a specified direction. The structure of the gas transportation actuator 11 will be described later. The gas sensor 12 is used for detecting VOCs of the gas to acquire plural monitored values of the VOCs. The microprocessor 13 is used for processing the monitored values generated by the gas sensor 12 to generate output data and controlling the actuation of the gas transportation actuator 11. The transmission module 14 transmits the output data generated by the microprocessor 13 to a connection device 200, so that the connection device 200 can display, store and transmit the information carried by the output data.

In some embodiments of the present disclosure, the connection device 200 may be a display device or a portable electronic device, and may have a wired communication module or a wireless communication module. Consequently, the connection device 200 can display a message on the screen as a warning notification to the user, or perform the warning notification by providing at least one selected from the group consisting of an image, a sound effect, a light effect and a vibration effect. Thereby, the user is notified to take protective measures. The transmission module 14 may be a wired transmission module or a wireless transmission module. The wired transmission module may be at least one selected form the group consisting of a USB transmission module, a mini-USB transmission module and a micro-USB transmission module. The wireless transmission module may be at least one selected from the group consisting of a Wi-Fi transmission module, a Bluetooth transmission module, a radio frequency identification (RFID) transmission module and a near field communication (NFC) transmission module. The connection device 200 and the transmission module 14 are not limited to the above embodiments and may be varied according to practical requirements.

Please refer to FIG. 1. In a step S104, the actuating-and-sensing module 1 guides the gas and performs VOC detection of the gas, wherein the gas transportation actuator 11 of the actuating-and-sensing module 1 transports and guides a specified amount of the gas (e.g., 1 liter to 14 liters per minute in average) to the gas sensor 12, and the gas sensor 12 detects VOCs of the gas and generates a monitored value (e.g., a VOC concentration value) according to a result of detection in each monitoring time intervals (e.g., each 5 minutes).

In this embodiment, in a step S106, the monitored values generated by the gas sensor 12 are calculated to obtain an average comparison value. More specifically, the microprocessor 13 averages all the monitored values obtained during a unit time period, thereby obtaining an average of those monitored values as the average comparison value. The average comparison value is for being served as a determination benchmark.

Then, in a step S108, the microprocessor 13 determines whether or not the average comparison value is greater than an injury threshold. If so, the actuating-and-sensing module 1 issues a warning notification, so that the user can be notified to take protective measures such as wearing a mask or escape. Above-mentioned injury threshold is defined by the upper limit of a safe exposure concentration of VOCs that a person can inhale and tolerate in the unit time period.

Figure 3:
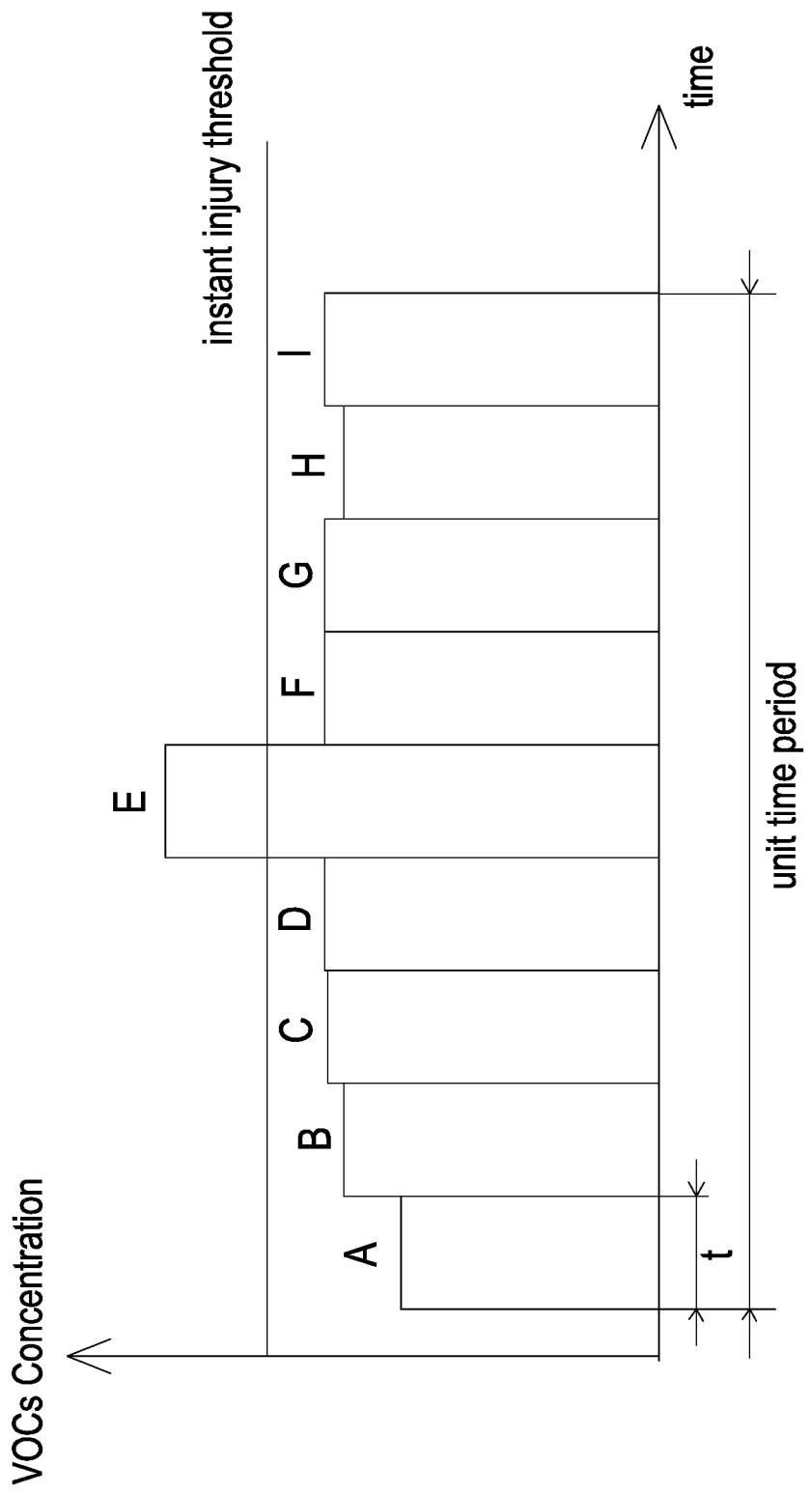
FIG. 3 schematically illustrates a monitoring result of a gas sensor of the actuating-and-sensing module within a unit time period according to the embodiment of the present disclosure.

FIG. 3 schematically illustrates a monitoring result of a gas sensor of the actuating-and-sensing module within a unit time period according to the embodiment of the present disclosure. As shown in FIG. 3, the monitored values of the VOCs sensed by the gas sensor 12 and corresponding to the monitoring time intervals t (e.g., the monitored values A, B, C, D, F, G, H and I) are not greater than an instant injury threshold, which is defined by the upper limit of a safe exposure concentration of VOCs that a person can inhale and tolerate in one monitoring time interval t. In these cases, the actuating-and-sensing module 1 does not issue the warning notification under control of the microprocessor 13. On the contrary, when the microprocessor 13 judges that any of the monitored values corresponding to the monitoring time interval t (e.g., the monitored value E) is greater than the instant injury threshold, the actuating-and-sensing module 1 issues the warning notification under control of the microprocessor 13. Consequently, the user can be warned in real time that the concentration of the VOCs in the environment is greater than the upper limit of the safe exposure concentration.

Meanwhile, the microprocessor 13 accumulates and calculates the monitored values obtained in every monitoring time interval t included in the unit time period, so as to obtain the average comparison value. As shown in FIG. 3, the plural monitoring time intervals t have been accumulated as a unit time period, and the average obtained by dividing the summation of the monitored values A, B, C, . . . , I corresponding to the monitoring time intervals t by the number of the monitoring time intervals t is defined as the average comparison value. The unit time period can be one hour, one month or one year. The microprocessor 13 averages the summation of the monitored values of the VOCs corresponding to the monitoring time intervals t within one hour, one month and one year as the first average comparison value, the second average comparison value and the third average comparison value, respectively. The microprocessor 13 compares the first average comparison value, the second average comparison value and the third average comparison value with an injury threshold, respectively. The injury threshold may be defined by the upper limit of the safe exposure concentration that a person can inhale and tolerate within one monitoring time interval t. When any one of the first average comparison value, the second average comparison value and the third average comparison value is determined greater than the injury threshold, the microprocessor 13 controls the actuating-and-sensing module 1 to issue a warning notification. Consequently, the user can be warned in different time stages that the accumulated amount of the VOCs achieves the upper limit of the safe exposure concentration.

Figure 4:
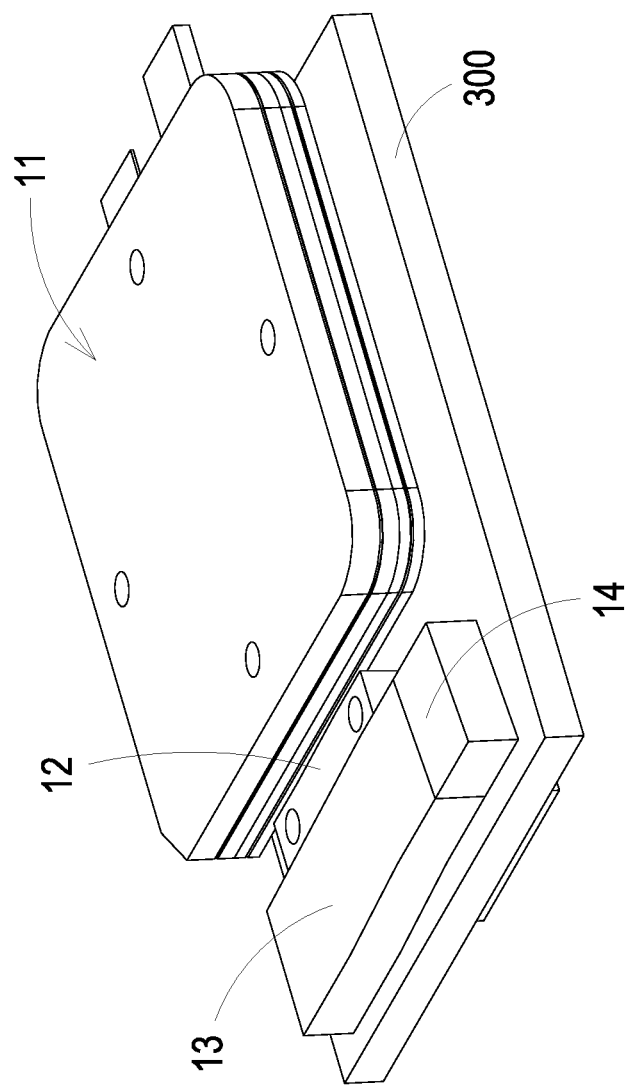
FIG. 4 is a schematic perspective view illustrating the actuating-and-sensing module according to the embodiment of the present disclosure.
Figure 5:
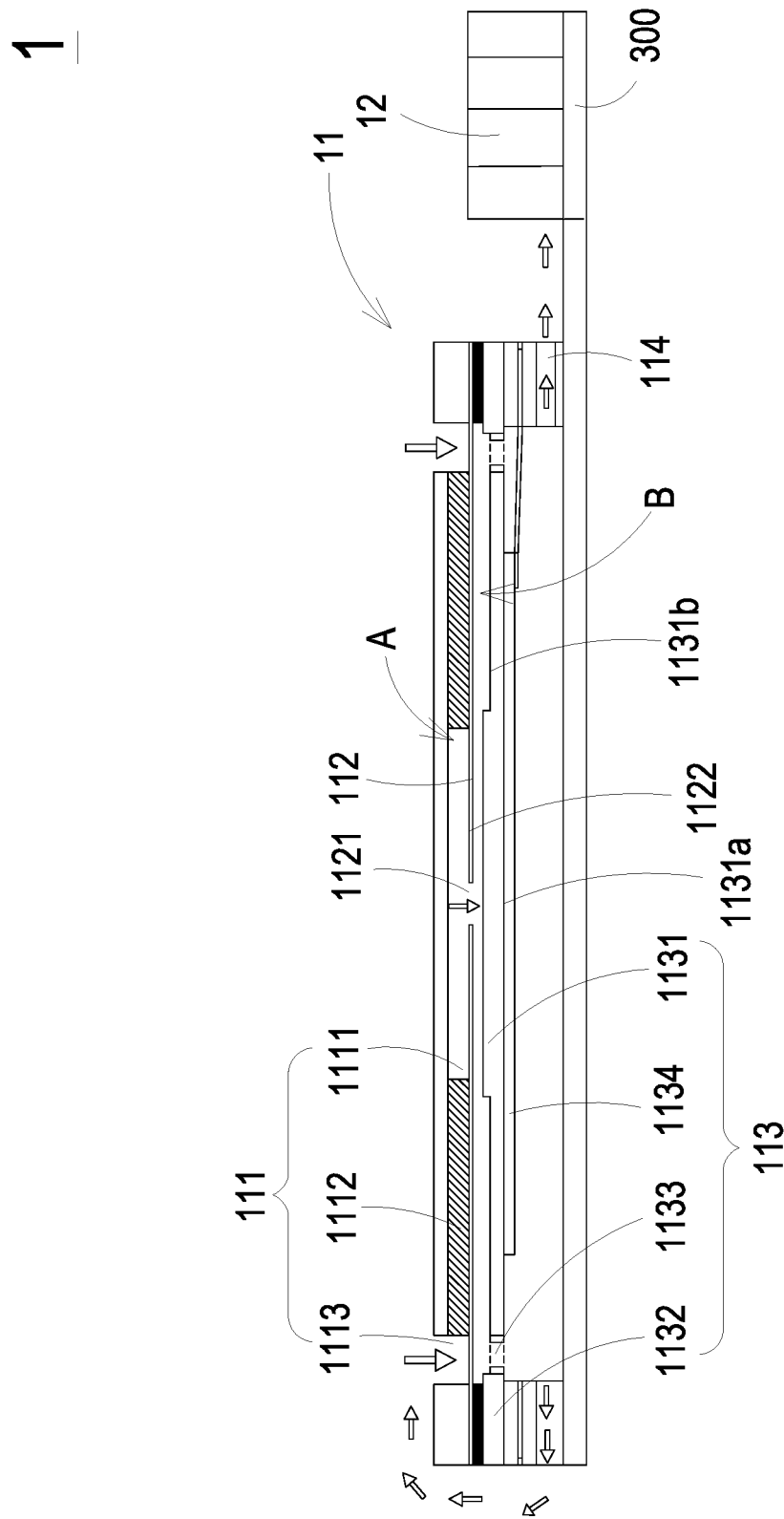
FIG. 5 is a schematic cross-sectional view illustrating the actions of the actuating-and-sensing module according to the embodiment of the present disclosure.

Please refer to FIGS. 4 and 5. FIG. 4 is a schematic perspective view illustrating the actuating-and-sensing module according to the embodiment of the present disclosure. FIG. 5 is a schematic cross-sectional view illustrating the actions of the actuating-and-sensing module according to the embodiment of the present disclosure. The gas transportation actuator 11, the gas sensor 12, the microprocessor 13 and the transmission module 14 of the actuating-and-sensing module 1 are disposed on a carrier 300. The gas transportation actuator 11 includes a gas inlet plate 111, a resonance plate 112 and a piezoelectric actuator 113. The gas inlet plate 111 includes a central cavity 1111, at least one convergence channel 1112 and at least one inlet 1113. The central cavity 1111 forms a convergence chamber A. After the gas is inhaled through the inlet 1113, the gas is guided through the convergence channel 1112, which is spatially corresponding to the inlet 1113, to the convergence chamber A. The resonance plate 112 has a central aperture 1121 spatially corresponding to the convergence chamber A. Moreover, the resonance plate 112 has a movable part 1122 surrounding the central aperture 1121.

The piezoelectric actuator 113 is corresponding in position to the resonance plate 112. The piezoelectric actuator 113 includes a suspension plate 1131, an outer frame 1132, at least one bracket 1133 and a piezoelectric plate 1134. The suspension plate 1131 has a first surface 1131a and a second surface 1131b. The suspension plate 1131 can be subjected to a bending vibration. The outer frame 1132 is arranged around the suspension plate 1131. The at least one bracket 1133 is connected between the suspension plate 1131 and the outer frame 1131, so that the bracket 1133 can elastically support the suspension plate 1131. The length of a side of the piezoelectric plate 1134 is smaller than or equal to the length of a side of the suspension plate 1131. Moreover, the piezoelectric plate 1134 is attached on the first surface 1131a of the suspension plate 1131 and is subjected to a deformation in response to an applied voltage so as to drive the suspension plate 1131 to undergo the bending vibration. There is a gap between the resonance plate 112 and the piezoelectric actuator 113 so as to define a first chamber B.

When the piezoelectric actuator 113 of the gas transportation actuator 11 is enabled, the piezoelectric plate 1134 is subjected to deformation so as to drive the suspension plate 1131 to vibrate in a reciprocating manner by using the bracket 1133 as a fulcrum. The piezoelectric actuator 113 is in resonance with the movable part 1122 of the resonance plate 112, so that the first chamber B is vibrated to generate a pressure gradient for inhaling the ambient gas into the inlet 1113 of the gas inlet plate 111 to form a gas flow. Then, the gas is transported to the convergence chamber A of the central cavity 1111 through the at least one convergence channel 1112. Then, the gas is transported to the first chamber B through the central aperture 1121 of the resonance plate 112. Then, the gas is transported downwardly to the region between the piezoelectric actuator 113 and the carrier 300 through the vacant space between the brackets 1133. Finally, the gas is ejected to the gas sensor 12 through an outlet channel 114. Since the gas is transported from the gas transportation actuator 11 to the gas sensor 12 at a specific transportation amount, the gas sensor 12 can monitor the gas consistent with the external environment so as to acquire the accurate detection result in real time.

From the above descriptions, the present disclosure provides a VOC detecting and warning method, which utilizes the gas transportation actuator of the actuating-and-sensing module to guide a specified amount of the gas to the gas sensor for monitoring the VOCs of the gas. Consequently, the accuracy of the VOC detection is increased. When the monitored value of the VOCs corresponding to the monitoring time interval is greater than an upper limit of a safe exposure concentration (e.g., the instant injury threshold), the actuating-and-sensing module issues a warning notification to warn the user that the VOC concentration value in the environment is too high. In addition, all the monitored values of the VOCs, which are sensed by the gas sensor and corresponding to the plural monitoring time intervals in a unit time period, are accumulated and averaged to obtain an average comparison value. If the average comparison value is greater than an upper limit of a safe exposure concentration (e.g., the injury threshold), the actuating-and-sensing module issues a warning notification to notify the user to take protective measures. Consequently, the cumulative damage caused by the exposure to VOCs in the located environment can be avoided.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A VOC detecting and warning method, comprising steps of:
    (a) providing an actuating-and-sensing module comprising a gas transportation actuator and a gas sensor, wherein the gas transportation actuator and the gas sensor are disposed on a carrier;
    (b) guiding a specified amount of gas to the gas sensor by an outlet channel of the gas transportation actuator and obtaining a monitored value generated according to a result of detecting a volatile organic compound of the specified amount of the gas in each monitoring time interval by the gas sensor;
    (c) calculating all the monitored values obtained in a unit time period to obtain an average comparison value; and
    (d) determining whether or not the average comparison value is greater than an injury threshold and issuing a warning notification by the actuating-and-sensing module if the average comparison value is greater than the injury threshold.

2. The VOC detecting and warning method according to claim 1, further comprising: issuing the warning notification by the actuating-and-sensing module if any of the monitored values is determined greater than an instant injury threshold.

3. The VOC detecting and warning method according to claim 1, wherein the specified amount of the gas guided by the gas transportation actuator is in the range between 1 liter and 14 liters per minute in average.

4. The VOC detecting and warning method according to claim 1, wherein the actuating-and-sensing module further comprises:
    a microprocessor processing the monitored values to generate output data and controlling the gas transportation actuator to actuate; and
    a transmission module transmitting the output data to a connection device, so that information carried by the output data is displayed, stored and transmitted by the connection device.

5. The VOC detecting and warning method according to claim 4, wherein the warning notification is performed by the connection device.

6. The VOC detecting and warning method according to claim 4, wherein the connection device is a display device with a wired communication module for displaying the warning notification.

7. The VOC detecting and warning method according to claim 6, wherein the transmission module is a wired transmission module, and the wired transmission module is at least one selected from the group consisting of a USB transmission module, a mini-USB transmission module and a micro-USB transmission module.

8. The VOC detecting and warning method according to claim 4, wherein the connection device is a display device with a wireless communication module for displaying the warning notification.

9. The VOC detecting and warning method according to claim 8, wherein the transmission module is a wireless transmission module, and the wireless transmission module is at least one selected from the group consisting of a Wi-Fi transmission module, a Bluetooth transmission module, a radio frequency identification transmission module and a near field communication transmission module.

10. The VOC detecting and warning method according to claim 4, wherein the connection device is a portable electronic device with a wireless communication module for performing the warning notification by providing an image, a sound effect, a light effect or a vibration effect.

11. The VOC detecting and warning method according to claim 1, wherein the gas transportation actuator comprises:
a gas inlet plate having at least one inlet, at least one convergence channel and a central cavity defining a convergence chamber, wherein the at least one inlet allows the gas to flow in, and wherein the convergence channel is spatially corresponding to the inlet and guides the gas flowing in the inlet to the convergence chamber;
a resonance plate having a central aperture and a movable part, wherein the central aperture is spatially corresponding to the convergence chamber and the movable part surrounds the central aperture; and
a piezoelectric actuator aligned with the resonance plate, wherein a gap is formed between the resonance plate and the piezoelectric actuator to define a first chamber, so that the gas flowing in the at least one inlet of the gas inlet plate is converged to the central cavity along the at least one convergence channel and flows into the first chamber through the central aperture of the resonance plate when the piezoelectric actuator is enabled, whereby the gas is further transported through a resonance between the piezoelectric actuator and the movable part of the resonance plate.

12. The VOC detecting and warning method according to claim 11, wherein the piezoelectric actuator comprises:
a suspension plate having a first surface and a second surface, wherein the suspension plate is permitted to undergo a bending vibration;
an outer frame arranged around the suspension plate;
at least one bracket connected between the suspension plate and the outer frame for elastically supporting the suspension plate; and
a piezoelectric plate, wherein a length of a side of the piezoelectric plate is smaller than or equal to a length of a side of the suspension plate, and the piezoelectric plate is attached on the first surface of the suspension plate, wherein when a voltage is applied to the piezoelectric plate, the suspension plate is driven to undergo the bending vibration.

13. A VOC detecting and warning method, comprising steps of:
(a) providing at least one actuating-and-sensing module comprising at least one gas transportation actuator and at least one gas sensor, wherein the at least one gas transportation actuator and the at least one gas sensor are disposed on a carrier;
(b) guiding a specified amount of gas to the gas sensor by an outlet channel of the gas transportation actuator and obtaining at least one monitored value generated according to a result of detecting at least one volatile organic compound of the specified amount of the gas in each monitoring time interval by the gas sensor;
(c) calculating all the monitored values obtained in at least one unit time period to obtain at least one average comparison value; and
(d) determining whether or not the average comparison value is greater than at least one injury threshold and issuing at least one warning notification by the actuating-and-sensing module if the average comparison value is greater than the injury threshold.

* * * * *